(12) United States Patent
Mascagni et al.

(10) Patent No.: US 6,984,632 B1
(45) Date of Patent: Jan. 10, 2006

(54) COMPLEXES OF PAROXETINE, WITH CYCLODEXTRINS OR CYCLODEXTRIN DERIVATIVES

(75) Inventors: Paolo Mascagni, Villasanta (IT); Giuseppe Bottoni, Bergamo (IT)

(73) Assignee: Italfarmaco S.p.A., Milan (IT)

( * ) Notice: Subject to any disclaimer, the term of this patent is extended or adjusted under 35 U.S.C. 154(b) by 15 days.

(21) Appl. No.: 09/763,581

(22) PCT Filed: Jun. 30, 2000

(86) PCT No.: PCT/EP00/06121

§ 371 (c)(1),
(2), (4) Date: Feb. 22, 2001

(87) PCT Pub. No.: WO01/02393

PCT Pub. Date: Jan. 11, 2001

(30) Foreign Application Priority Data

Jul. 1, 1999 (IT) ............................... MI99A1459
Nov. 17, 1999 (IT) ............................... MI99A2406

(51) Int. Cl.
*A61K 31/724* (2006.01)
*A61K 31/4525* (2006.01)

(52) U.S. Cl. .......................... 514/58; 514/317; 514/321
(58) Field of Classification Search ................. 514/58, 514/317, 321; 546/197, 216, 227, 240
See application file for complete search history.

(56) References Cited

U.S. PATENT DOCUMENTS

| 4,721,723 A | | 1/1988 | Barnes et al. ............... 514/321 |
| 5,672,612 A | | 9/1997 | Ronsen et al. .............. 514/338 |
| 5,874,447 A | * | 2/1999 | Benneker et al. ........... 514/321 |
| 5,904,929 A | * | 5/1999 | Uekama et al. ............. 424/443 |

FOREIGN PATENT DOCUMENTS

| EP | 810224 | 12/1997 |
| WO | WO9831365 | 7/1998 |
| WO | WO9916440 | 4/1999 |
| WO | WO9926625 | 6/1999 |

* cited by examiner

*Primary Examiner*—Leigh C. Maier
(74) *Attorney, Agent, or Firm*—Abelman, Frayne & Schwab

(57) ABSTRACT

Complexes of paroxetine, as free base or salt, with a cyclodextrin or a cyclodextrin derivative having a molar ratio between paroxetine and cyclodextrin ranging from 1:0.25 to 1:20, suitable for use in liquid and solid pharmaceutical compositions for oral and parenteral administration.

24 Claims, 11 Drawing Sheets

COMPLEXES OF PAROXETINE, WITH CYCLODEXTRINS OR CYCLODEXTRIN DERIVATIVES

PRIOR ART

Paroxetine is an organic base having the following formula:

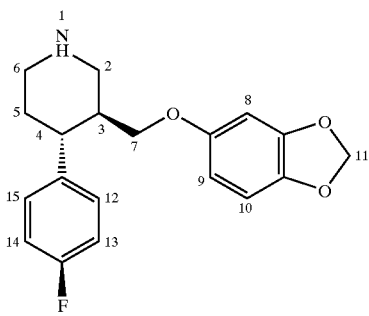

It is used as a therapeutic agent in several pathological forms and particularly in depression and Parkinson's disease because of its inhibitory activity on the neuronal recaptation of serotonin (5-HT).

In the pharmaceutical applications paroxetine is commonly used in its crystalline form of hemihydrated hydrochloride (U.S. Pat. No. 4,721,723). However, the poor solubility in water of this compound limits the possibility to prepare liquid pharmaceutical forms containing a suitable concentration of active principle while solid pharmaceutical forms show a limited bioavailability and a remarkable variability in plasmatic levels in different patients.

Paroxetine hydrochloride in an amorphous form, having the advantage of a faster solubilisation, is disclosed in patents EP810224, WO 98/31365, U.S. Pat. No. 5,672,612 and WO 99/16440.

EP810224 and WO 98/31365 disclose a preparation procedure but they do not point out the particular advantages of it, except the faster solubilisation due to the amorphous state of the product.

In U.S. Pat. No. 5,672,612 it is claimed that paroxetine in an amorphous form is stable if present in the composition with ethanol at a % by weight of up to 10% and preferably of about 1–4%. However, such a content of ethanol is not commonly acceptable and desirable in a pharmaceutical composition.

In WO 99/16440 other compositions containing paroxetine hydrochloride are described, starting from the same preparation of paroxetine HCl in ethanol, wherein a variety of compounds such as acids, hydroxyacids and polyhydroxylated substances might allow to obtain the same stabilising effect. In the Patent Application it is claimed that all the above compounds should have the same effect. Among the compositions described, a composition comprising a cyclodextrin and in particular hydroxypropyl-β-cyclodextrin is cited and claimed. However, the complex and its characteristics are not described. Furthermore, the problem relating to the presence of ethanol in the formulation remain unaltered. In fact said compositions are prepared by processes comprising:

dissolution of paroxetine base in absolute ethanol;
preparation of a hydrochloric acid solution in absolute ethanol;
addition of the hydrochloric acid solution in absolute ethanol to the solution of paroxetine base;
stirring in order to obtain a composition of paroxetine hydrochloride in ethanol; adding of a polyhydroxylated compound, if any; and
drying of the above mentioned composition.

Since said processes operate in ethanol, they necessarily bring to a final product containing significant amounts of this solvent and this results in obvious drawbacks from the pharmaceutical point of view.

The use of ethanol is also not convenient from the point of view of the process. Paroxetine salts, due to their ionic characteristics, are not directly absorbed by the gastrointestinal wall but they must first transform in the non salified paroxetine which, being lipophylic, is able to go through the gastrointestinal mucosa.

The transformation process is linked to the equilibrium constant represented by the formula: paroxetine HX $\rightleftarrows$ paroxetine+HX and it is influenced by the pH of the medium.

On the other hand, paroxetine as free base is unsuitable to be used as such for the manufacturing of pharmaceutical forms as it consists of a dense liquid having oily characteristics or of a waxy solid. Moreover, it easily decomposes becoming oxidized and its solubility in water is very low.

Actually, in Patent Application WO99/26625 capsules containing paroxetine as free base or as a pharmaceutically acceptable salt in a liquid or solid carrier are claimed.

However, the several reported compositions (Examples 1–30) all refer to the use of paroxetine hydrochloride, while the subsequent Examples (Examples 31–44) refer to paroxetine liquid formulations (it is not specified if as free base or as salt) in Pharmasolve, oil and lipids.

As solid or semisolid carriers fats, waxes and filmogenic or thermoplastic polymers are cited.

SUMMARY OF THE INVENTION

We have now found that the problems of the prior art can be solved by complexes of paroxetine, as free base or as salt, with a cyclodextrin or a cyclodextrin derivative.

The complexes according to the present invention may have the form of a flowing powder, they show a high chemical stability, an improved solubility in water and are suitable for the preparation of liquid or solid pharmaceutical compositions. Furthermore, paroxetine present in said complexes shows a pH-independent dissolution behaviour.

Said complexes may be prepared by a process comprising the following steps: paroxetine, as free base or as salt, a cyclodextrin or a cyclodextrin derivative and water are mixed;
the obtained mixture is stirred in order to obtain an homogeneous solution or dispersion and stirring is continued until formation of a complex;
the solid is filtered and then dried or the solution or dispersion is dried and the solid recovered.

DETAILED DESCRIPTION OF THE INVENTION

Figure 1:
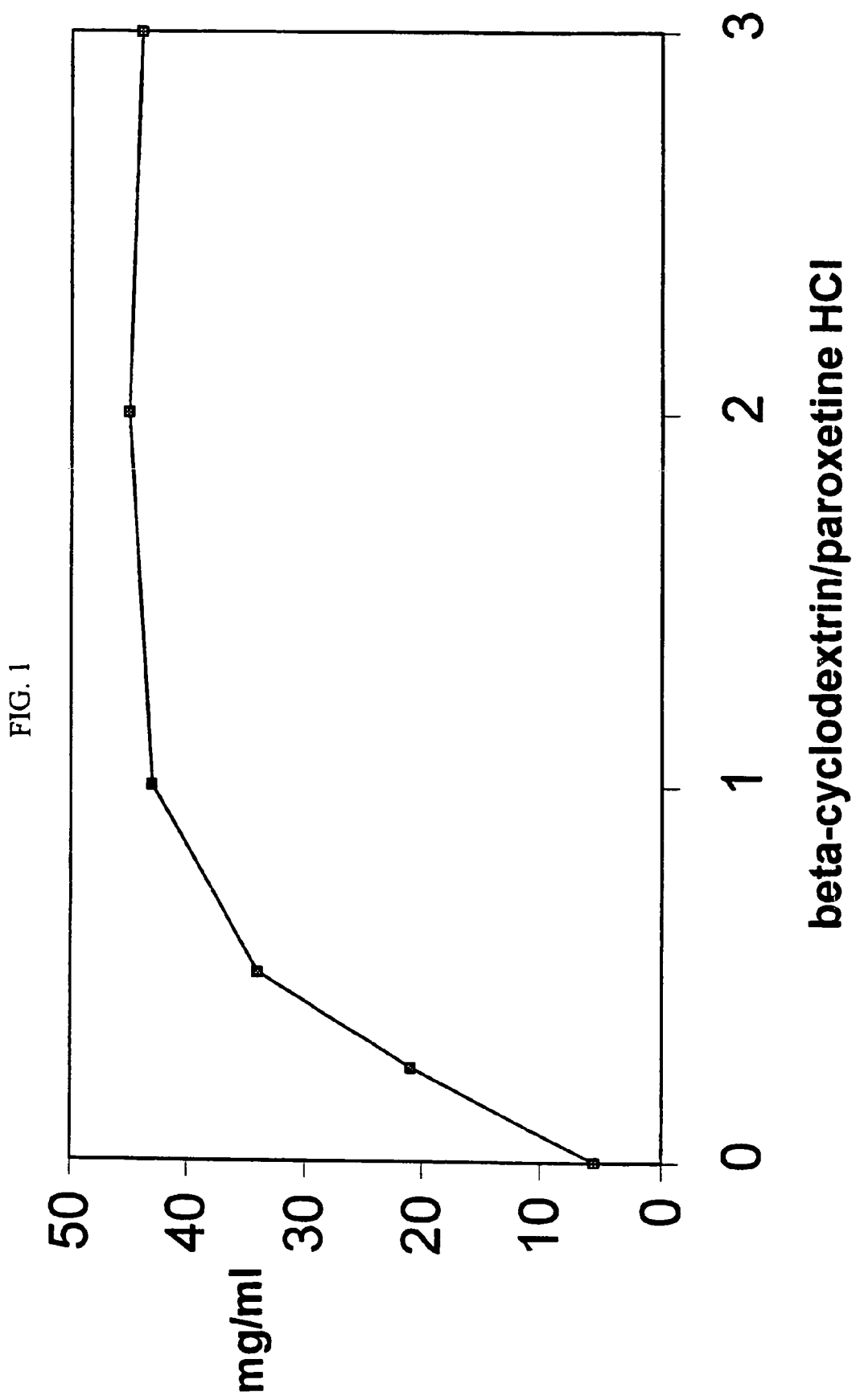
FIG. 1 shows the solubility of complexed paroxetine HCl at different molar ratios between β-cyclodextrin and paroxetine HCl.

The present invention refers to complexes of inclusion of paroxetine, as free base or as salt, with a cyclodextrin or a derivative thereof.

Said complexes are preferably prepared according to a process characterised by the following steps:
  (a) paroxetine, as free base or as salt, a cyclodextrin or a cyclodextrin derivative and water are mixed;
  (b) the obtained mixture is stirred in order to obtain an homogeneous solution or dispersion and stirring is continued until formation of the complex; and
  (c) the water is partially removed in order to obtain a solid complex with a desired water content.

Preferably, the complexes of the invention have a water content between 1 and 20%, preferably between 2 and 15%, by weight.

Paroxetine may be used as a free base or as a salt with an organic or an inorganic acid.

Preferably said organic or inorganic acid is selected from the group comprising acetic acid, maleic acid, hydrochloric acid and methanesulfonic acid. Among these, hydrochloric acid is particularly preferred.

Paroxetine base may be used either as a waxy solid or as a oily liquid.

Preferably, said cyclodextrin is α-, β-, or γ-cyclodextrin, in anhydrous or hydrated form.

Said cyclodextrin derivative is preferably selected from the group consisting of eptakis (2-6-di-O-methyl)-β-cyclodextrin, (2,3,6-tri-O-methyl)-β-cyclodextrin, monosuccinyl eptakis (2,6-di-O-methyl)-β-cyclodextrin, 2-hydroxypropyl-β-cyclodextrin, sulphated cyclodextrin or cyclodextrin containing aminoalkyl groups.

Preferably, in the present invention β-cyclodextrin and 2-hydroxypropyl-β-cyclodextrin are used.

Preferably, in step a) 1 to 100 g of cyclodextrin or cyclodextrin derivative are used per liter of water.

Preferably, paroxetine as free base or as salt are used in such a quantity as to obtain complexes with a molar ratio between paroxetine and cyclodextrin ranging from 1:0.25 to 1:20 and preferably from 1:0.5 to 1:2.

Slightly different operative patterns may be used when preparing complexes of paroxetine base and of a paroxetine salt.

In detail, when preparing a complex with paroxetine base, step a) is preferably carried out according to the following steps:
  $a_1$) a cyclodextrin or a cyclodextrin derivative is added to water;
  $a_2$) the solution or dispersion of step $a_1$) is kept under stirring for a time from 30 to 180 minutes at a temperature between 25° C. and 50° C.; and
  $a_3$) paroxetine base is dispersed in the solution or dispersion of step $a_2$).

When preparing a complex with a paroxetine salt, step a) is preferably carried out according to the following steps:
  $a_1$) paroxetine base is salified with an organic or inorganic acid; and
  $a_2$) a cyclodextrin or a cyclodextrin derivative is added under stirring to the salified paroxetine.

The salification of paroxetine base can be carried out using different procedures. For example, paroxetine base may be dispersed in water under stirring and an aqueous solution of the selected acid may be added to the dispersion until formation of a solution. Alternatively, paroxetine base may be added to an aqueous solution of the selected acid.

When preparing both types of complexes, step b) is preferably carried out by mechanical stirring or by ultrasounds. Preferably, in order to allow formation of the complex, stirring is carried out at a temperature 25° and 50° C. for a time up to 48 hours, preferably between 3 and 24 hours.

Step c) is usually carried out by freeze drying, vacuum drying or drying under an inert gas flux. Preferably, vacuum drying is carried out at a temperature from 20 to 40° C. and drying under an inert gas flux at a temperature from 5 to 40° C.

Preferably, when preparing a complex of paroxetin base, step c) can also be carried out according to the following steps:
  $c_1$) the dispersion of step c) is cooled and maintained at a temperature between 4° C. and 20° C. for 1 to 20 hours;
  $c_2$) the precipitate obtained in step $c_1$) is recovered by filtration; and
  $c_3$) the solid product recovered in step $c_2$) is dried under vacuum or under an inert gas flux until the desired water content is reached.

As will be described in detail in the Examples below, different drying procedures lead to complexes having different characteristics: complexes in an amorphous state are obtained by freeze drying, while crystalline complexes are obtained by vacuum drying.

As an alternative to the above disclosed process, complexes containing paroxetine base may be prepared by slowly adding to a cyclodextrin or a derivative thereof paroxetine in the form of an oily liquid in a mixer for powders kept under stirring for a time from 3 to 24 hours, at a temperature from 25 to 50° C.

Also in this case the treatment in the mixer for powders may be substituted with an ultrasonic treatment.

As a further alternative, complexes containing paroxetine base can be prepared by formation of a slurry consisting of a cyclodextrin or a derivative thereof, paroxetine base and water, wherein the amount of the latter compound ranges from 20 to 100% of the weight of the solid substances. The slurry is then mixed and dried as described above.

The product obtained through any of the above processes is then usually sieved on a 250 μm sieve in order to obtain a product with a particle size distribution suitable for further processing.

The complexes of the present invention are new products as proved by the results of the characterisations reported below.

In particular these products have the following characteristics:
- the form of a flowing powder, a suitable physical state for the production of pharmaceutical forms;
- a higher solubility in water with respect to the non-complexed product which may give a decreased variability in plasmatic levels;
- a greater stability in comparison with the non-complexed product;
- by NMR characterization they show a positive variation of the chemical shift of many protons of paroxetine and a negative variation of the protons of cyclodextrin present in its cavity;
- by differential thermal analysis (DSC) the complexes with paroxetine base show absence of the decomposition peak of paroxetine base between 260° and 300° C. while the complexes with a paroxetine salt show absence of thermal events at temperatures corresponding to the peak of fusion of the relative non-complexed salt.

Furthermore, thanks to the process used the products of the present invention are free from organic solvents, such as ethanol, which are present in many preparations of the known technique.

Thanks to their characteristics, the products of the present invention may be used for the preparation of solid and liquid pharmaceutical compositions for oral and parenteral administration with improved effects in the treatment of depression and Parkinson's disease and other pathologies curable by administration of paroxetine. Said compositions comprise a pharmaceutically effective dose of a complex according to the present invention in mixture with pharmaceutically acceptable diluents or excipients.

The present invention also refers a therapeutic method for the treatment of subjects suffering from depression or Parkinson's disease, and from any other pathology curable with paroxetine, consisting in the administration of said complexes in an amount corresponding to 5–40 mg per day of paroxetine orally and corresponding to 1–20 mg per day of paroxetine parenterally.

The present invention may be further understood with reference to the following Examples.

EXAMPLE 1

1 g of paroxetine base is dispersed in 150 g of deionized water under stirring. A solution of 0.11 g of HCl in 28 g of water is added to the dispersion under stirring and stirring is continued until paroxetine is completely solubilised.

The pH of the solution is about 6.

3.5 g of β-cyclodextrin in powder are added to the solution and the obtained dispersion is heated to 40° C. under nitrogen flux and with vigorous stirring for 3 hours.

An opalescent solution is obtained containing a little amount of undissolved residue which is removed by filtration through a cellulose acetate filter having 0.45 μm porosity.

The obtained solution is freeze-dried and 4.3 g of a product with a molar ratio between paroxetine HCl and β-cyclodextrin of 1:1 and with a water content of 5.4% by weight are obtained.

The product has been characterised as described below.

EXAMPLES 2–5

These Examples have been carried out according to the method described in Example 1 using amounts of reacting substances such as to obtain final products with the following molar ratios between β-cyclodextrin and paroxetine HCl:

TABLE 1

| Example N. | Molar Ratio |
| --- | --- |
| 2 | 0.25:1 |
| 3 | 0.50:1 |
| 4 | 2.0:1 |
| 5 | 3.0:1 |

The products obtained from these examples and from Example 1 have all been characterised for their solubility in water compared to non-complexed paroxetine HCl, as described below.

EXAMPLE 6

1 g of paroxetine base is suspended in a solution consisting of 25 g of deionized water and 2.8 ml of 1 N HCl and, under vigorous stirring, 3.5 g of β-cyclodextrin in powder are added.

The mixture is kept under stirring for 24 hours at 25° C. under nitrogen flux.

The obtained mixture is partially concentrated and finally vacuum dried at 25° C. for 48 hours.

4.4 g of a product with a molar ratio between paroxetine HCl and β-cyclodextrin of 1:1 and with a water content of 5.4% are obtained.

EXAMPLE 7

Example 1 has been repeated with the difference that acetic acid (110 mg) instead of hydrochloric acid has been used. 4.3 g of the relative complex have been obtained.

EXAMPLE 8

Example 1 has been repeated with the difference that 2-hydroxypropyl-β-cyclodextrin (4.0 g) instead of β-cyclodextrin has been used.

4.7 g of the relative complex have been obtained.

The products of the Examples 7 and 8 have been characterised as described for the product of Example 1 with similar results.

EXAMPLE 9

In a glass reactor 3.5 g of β-cyclodextrin are solubilised in 50 ml of deionized water at 45° C.

1 g of paroxetine base is dispersed in the obtained solution and the suspension is kept under stirring at 45° C. for a 5 hours.

The obtained suspension is cooled to 15° C. and a precipitate is recovered by filtration on a cellulose acetate filter.

The obtained product is dried in a stove under vacuum at 40° C. for 12 hours, to a 9% residual content of water, determined by the Karl Fisher method.

4.3 g of product in the form of a flowing powder are obtained wherein the molar ratio between basic paroxetine and β-cyclodextrin is about 1:1.3, as determined by spectrophotometry at 293 nm in comparison with a standard solution of paroxetine base.

The product has been sieved through a 250 μm sieve and characterised as described below.

EXAMPLE 10

In a mixer for powders 20 g paroxetine base in form of oil are slowly added under stirring to 70 g of β-cyclodextrin.

The stirring is continued for 12 hours obtaining an homogeneous mixture.

86 g of product in the form of a flowing powder are obtained which are sieved through a 250 μm sieve.

The product has a molar ratio between basic paroxetine and β-cyclodextrin of about 1:1.

The product has been characterised as described later for the product of Example 9 with similar results.

EXAMPLE 11

Example 9 has been repeated with the difference that 2-hydroxypropyl-β-cyclodextrin (4.0 g) has been used instead of β-cyclodextrin.

4.7 g of product in form of a flowing powder have been obtained.

Also this product has been characterised as described for the product of Example 9 with similar results.

EXAMPLE 12

Characterisation of the Complexes of the Invention

A) Solubility

The solubility of the products obtained in Examples 1–5 and 9 has been evaluated in comparison with that of the non-complexed paroxetine base or paroxetine HCl i) Complexes of Example 1–5

A solubility test was carried out on an amount of the complexes of Examples 1 to 5 corresponding 500 mg of paroxetine HCl and, as a comparison, on 500 mg of non-complexed paroxetine HCl.

Each sample was introduced into a container containing 5 ml of deionized water. The containers, closed with a plug were then set under stirring in a thermostatic bath at 25° C. for 24 hours.

The obtained suspensions were then filtered through a cellulose acetate filter and analysed by spectrophotometry at 295 nm, in comparison with a standard solution of paroxetine.

The results obtained are reported in FIG. 1 wherein the solubility of paroxetine HCl (in mg/ml) is represented as a function of the molar ratio between β-cyclodextrin and paroxetine HCl.

From the plot one may note that while the solubility of the non-complexed paroxetine HCl is 5 mg/ml, as reported in literature, the solubility of the complexes is higher and increases with the increase of the molar ratio between β-cyclodextrin and paroxetine HCl, reaching a solubility up to 45 mg/ml at a 1:1 ratio.

ii) Complex of Example 9

5 g of the product of Example 9 were added to 10 ml of deionised water and kept under stirring for 4 hours at room temperature.

The suspension was then filtered through a cellulose acetate filter in order to remove the undissolved product.

The solution was analysed by 293 nm spectrophotometry against a standard solution of paroxetine base.

The content of paroxetine base in the solution was 2.3 mg/ml. As a comparison, the solubility of the non-complexed paroxetine base was also measured. A solubility of 0.3 mg/ml was found.

B) NMR characterisation

This characterisation has been carried out on the products of Example 1 and 9 in comparison with Paroxetine and Paroxetine HCl, by $_1$HNMR 200 MHz in $D_2O$.

The results are reported in Table 2 and 3 wherein one may notice the chemical shift positive variation of many protons of paroxetine and the chemical shift negative variation of the proton of β-cyclodextrin inside its cavity.

This proves that the product consists of a complex of paroxetine base or salt with β-cyclodextrin.

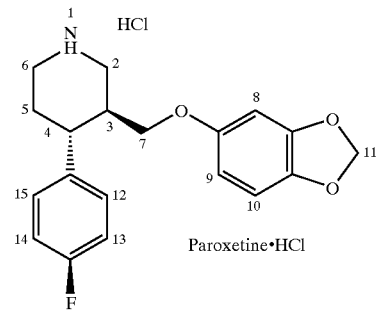

Paroxetine·HCl

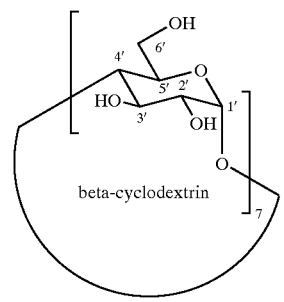

beta-cyclodextrin

TABLE 2

| Protons | multi-plicity | Paroxetine HCl | Paroxetine base | Product of Example 1 | Product of Example 9 |
|---|---|---|---|---|---|
| H$_{12, 15}$ | dd (2H) | 7.18 (−0.01) | 7.18 (−0.01) | 7.25 (0.06) | 7.25 (0.06) |
| H$_{13, 14}$ | t (2H) | 6.97 (−0.02) | 6.97 (−0.02) | 7.09 (0.10) | 7.09 (0.10) |
| H$_{10}$ | d (1H) | 6.60 (−0.02) | 6.60 (−0.02) | 6.64 (0.02) | 6.64 (0.02) |
| H$_8$ | d (1H) | 6.32 (−0.01) | 6.32 (−0.01) | 6.47 (0.14) | 6.47 (0.14) |
| H$_9$ | dd (1H) | 6.11 (−0.02) | 6.11 (−0.02) | 6.09 (−0.04) | 6.09 (−0.04) |
| H$_{11}$ | s (2H) | 5.79 (−0.02) | 5.79 (−0.02) | 5.86 (1H) (0.05) 5.80 (1H) (−0.01) | 5.86 (1H) (0.05) 5.80 (1H) (−0.01) |
| H4 | t (1H) | 3.08 (—) | | 3.20 (0.12) | |
| H6a | dt (1H) | 2.85 (−0.02) | | 2.98 (0.11) | |
| H3 | m (1H) | 2.34 (—) | | 2.44 (0.10) | |

TABLE 3

| Proton | Multiplicity | β-cyclodextrin | Product of Example 1 | Product of Example 9 |
|---|---|---|---|---|
| H$_{3'}$ | t (1H) | 3.94 | 3.81 (−0.13) | 3.81 (−0.13) |
| H$_{2'}$ | dd (1H) | 3.62 | 3.63 (0.01) 3.64 (0.02) | 3.63 (0.01) 3.64 (0.02) |

C) Differential Thermal Analysis (DSC)

DSC tests have been carried out on the products prepared In Example 1, 7, 8 and 9, using the following conditions:

| | |
|---|---|
| Equipment: | Perkin Elmer DSC7 |
| Temperature Range: | 50–300° C. (Examples 1 and 9) |
| | 50–200° C. (Examples 7 and 8) |
| Heating Rate: | 10° C./minute | i) Complex of Example 1

Figure 2:
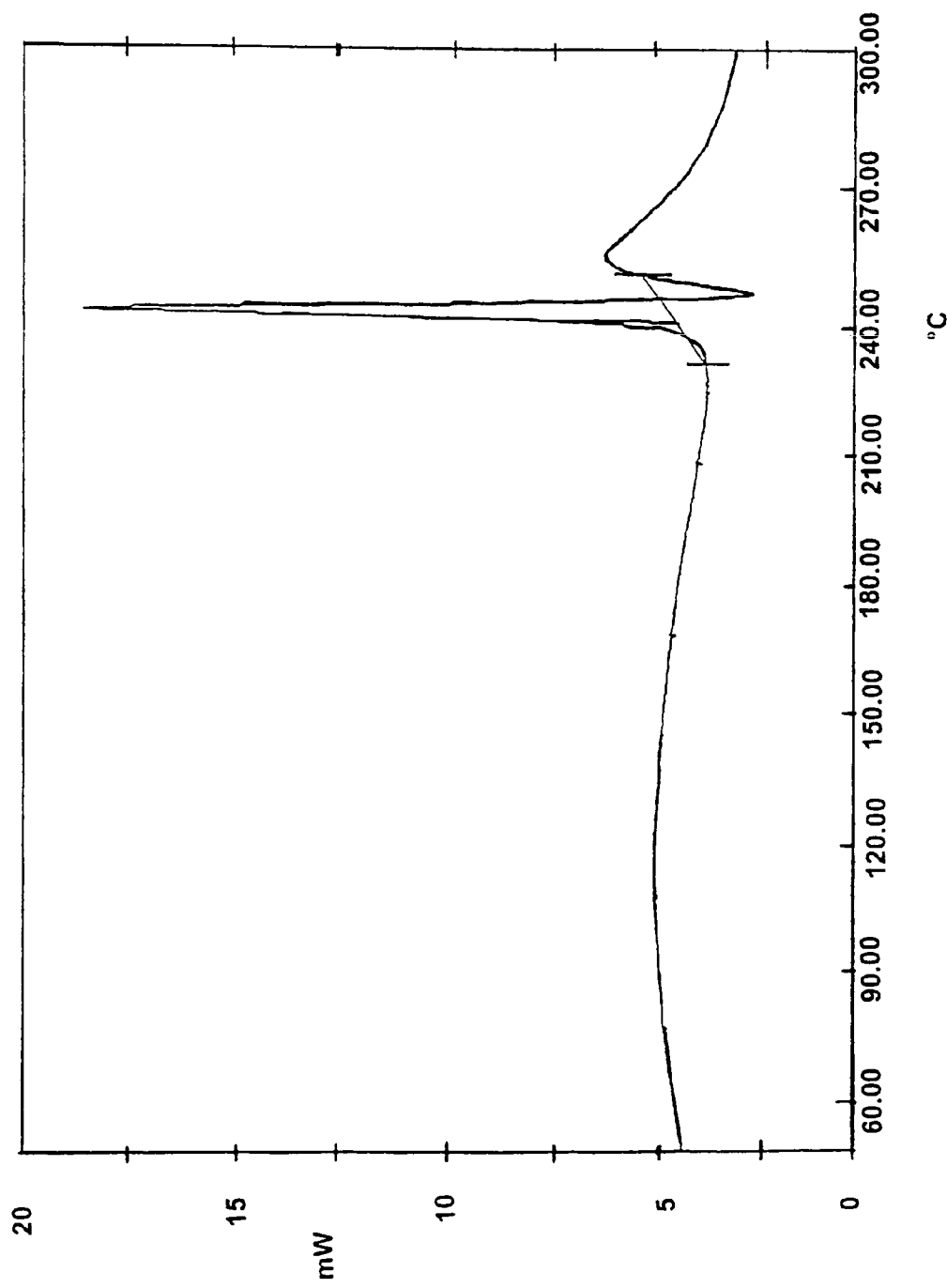
FIG. 2 shows the thermogram obtained in a DSC test carried out on a complex between paroxetine HCl and β-cyclodextrin 1 hour after preparation.

A DSC test was first carried out on the product prepared in Example 1 one hour after preparation. The obtained thermogram is reported in FIG. 2 and it is characterised by the absence of thermal events in the 100–200° C. range while it shows a peak between 230 and 250° C.

Considering that the commonly used paroxetine HCl (hemihydrated form) has a melting point equal to 143.5° C. and that the other known forms of paroxetine HCl have melting points ranging from 117 to 164° C., one may conclude that the product of the Example 1 is a new product.

Figure 3:
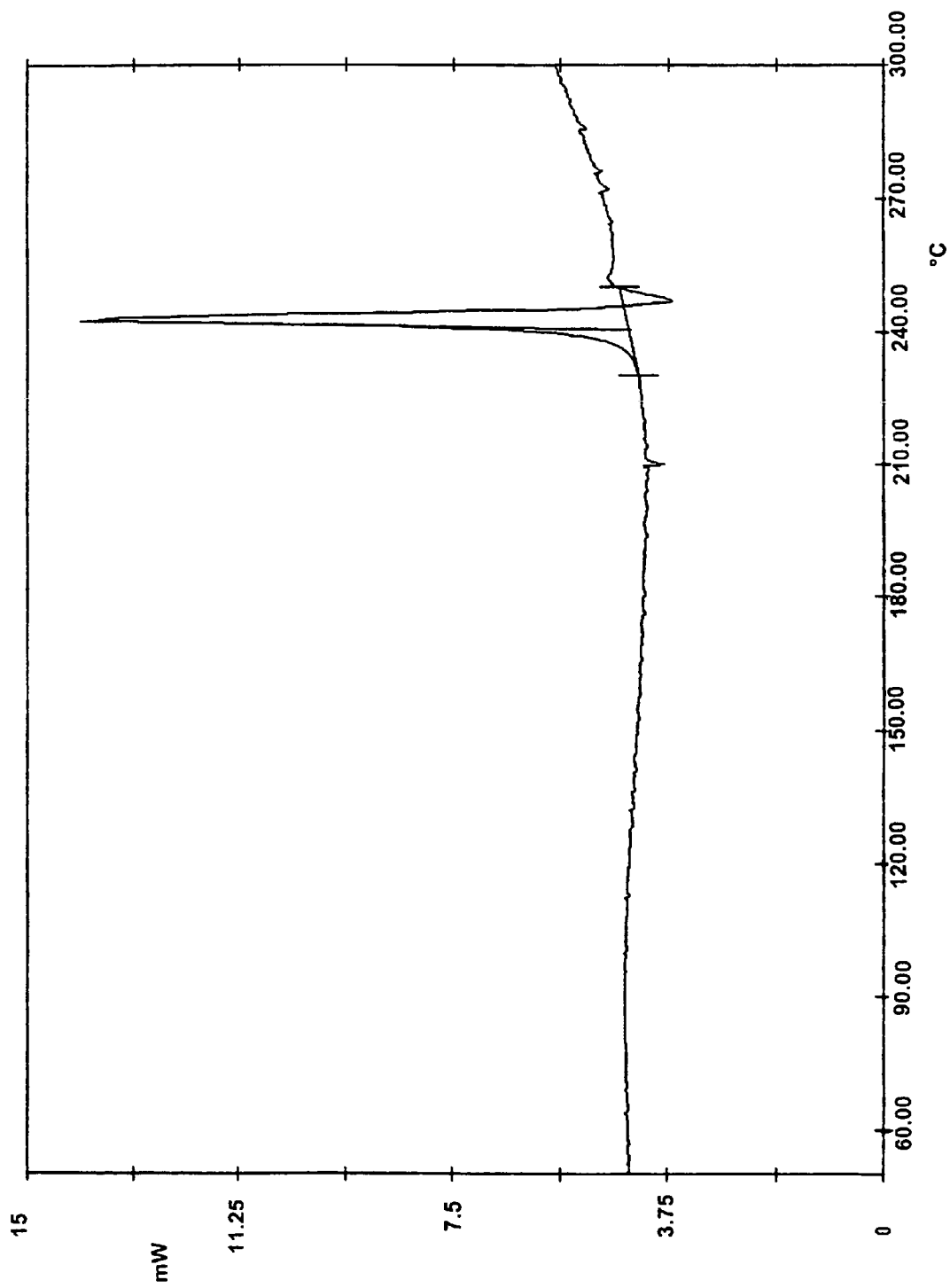
FIG. 3 shows the thermogram obtained in a DSC test carried out on a complex between paroxetine HCl and β-cyclodextrin 7 days after preparation.
Figure 4:
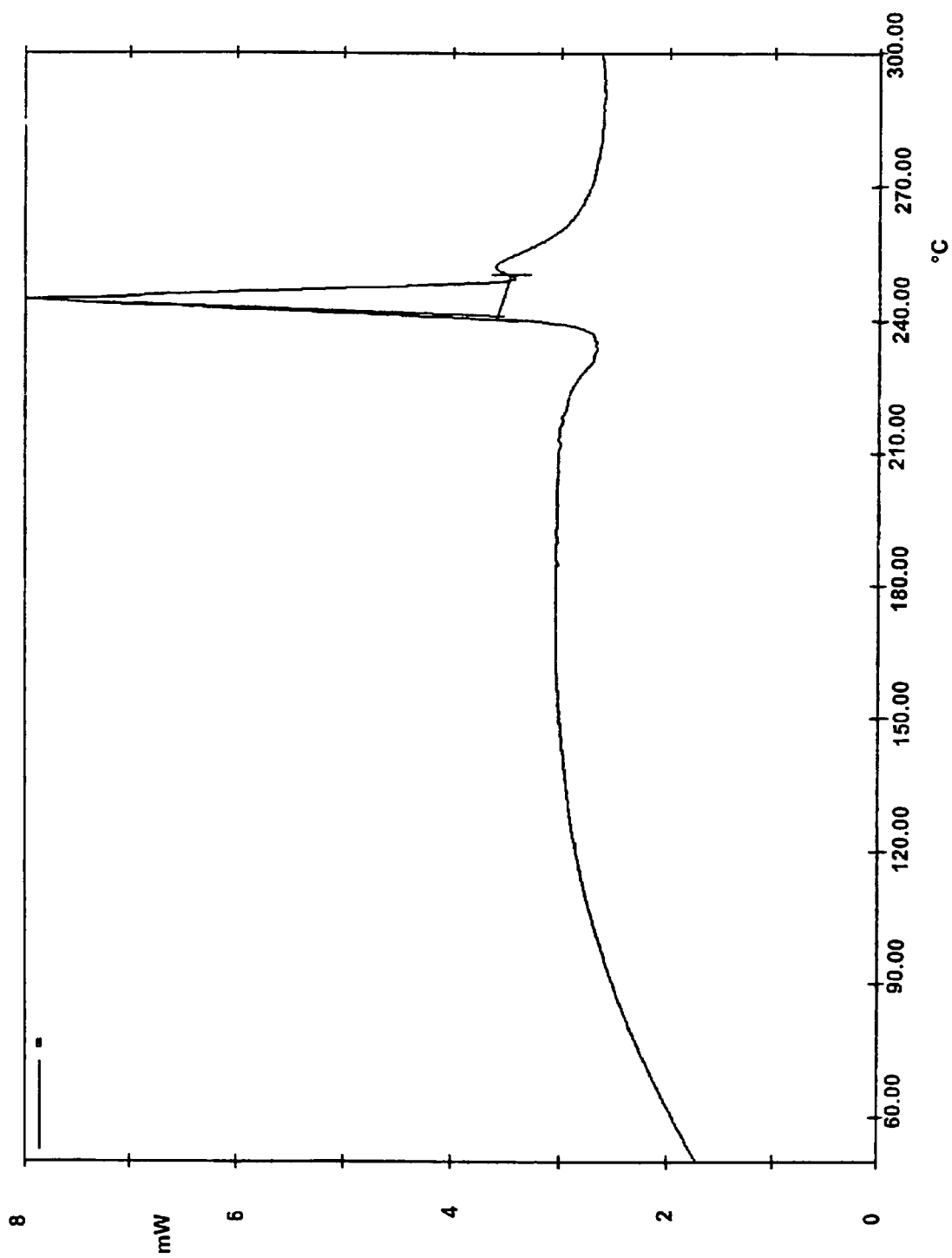
FIG. 4 shows the thermogram obtained in a DSC test carried out on a complex between paroxetine HCl and β-cyclodextrin 3 months after preparation.

The DSC analysis was then repeated on the same product after storing at 25° C. and 60% relative humidity for 7 days (FIG. 3) and 3 months (FIG. 4), respectively. The thermograms show that the product is stable in time and it is not transformed into known crystalline forms of paroxetine HCl.

ii) Complex of Example 7

Figure 5:
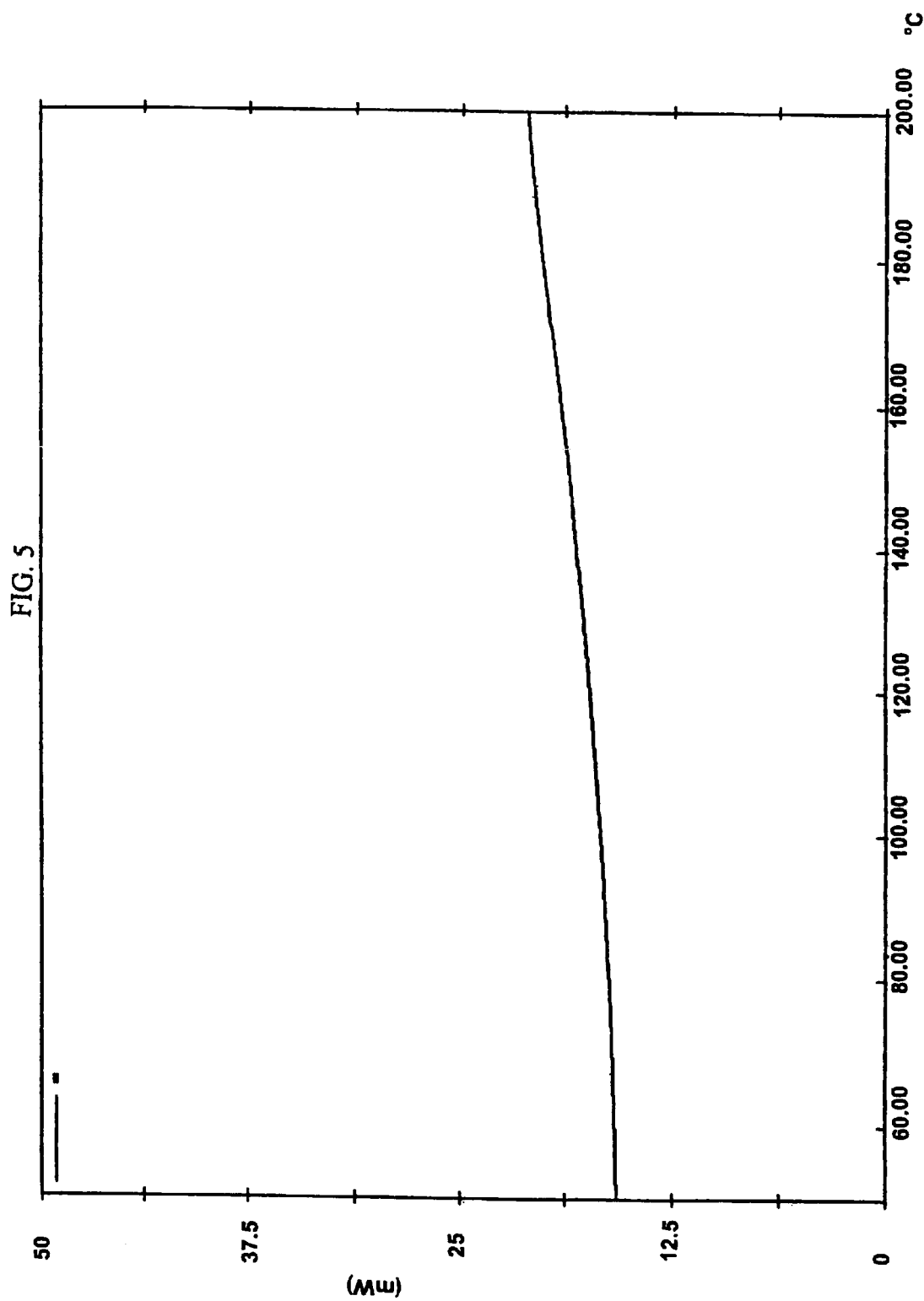
FIG. 5 shows the thermogram obtained in a DSC test carried out on a complex between paroxetine acetate and β-cyclodextrin two weeks after preparation.

A DSC test was carried out on the complex of Example 7 two weeks after preparation. The thermogram (FIG. 5) shows absence of thermal events at temperatures below 200° C.

iii) Complex of Example 8

Figure 6:
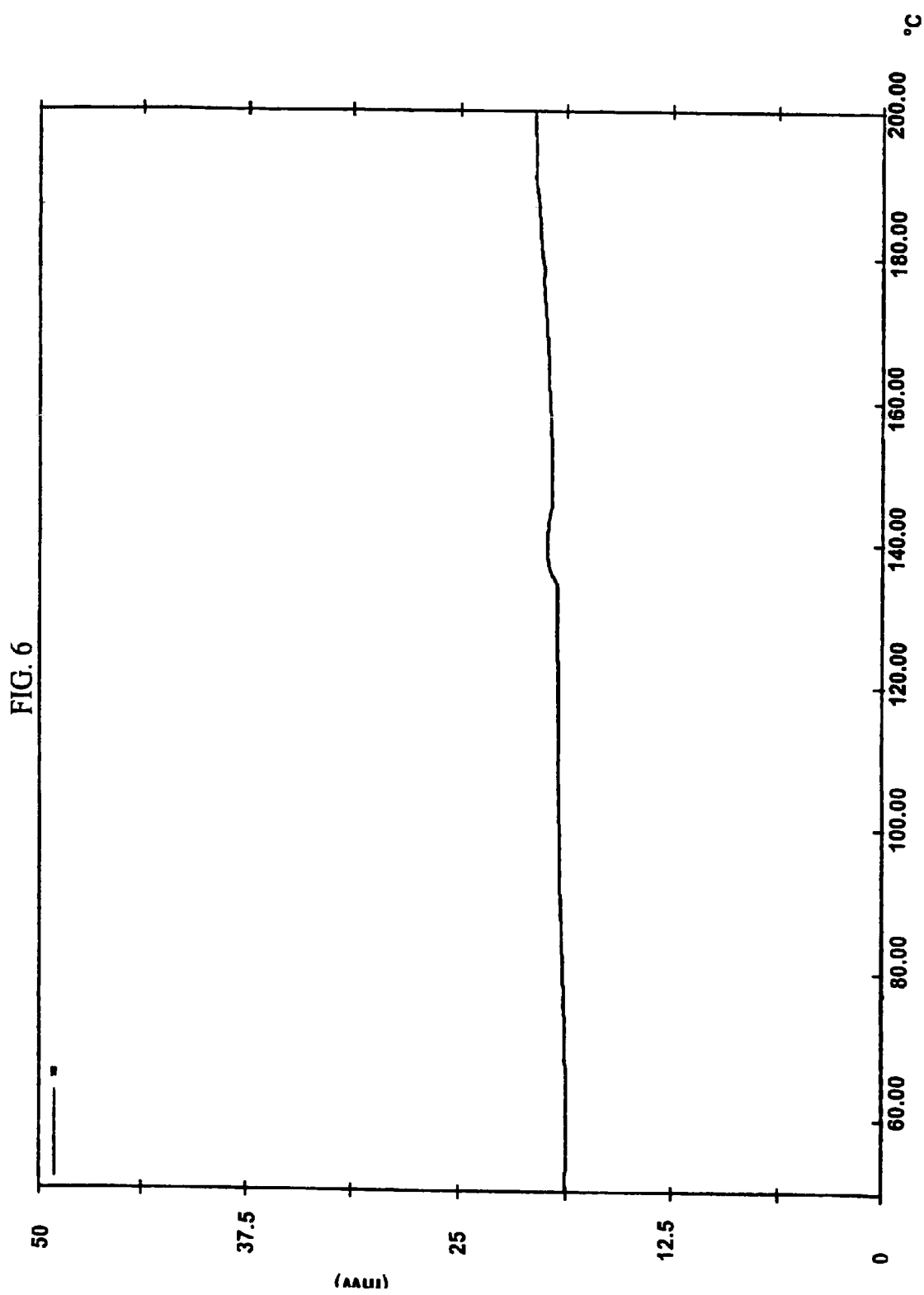
FIG. 6 shows the thermogram obtained in a DSC test carried out on a complex between paroxetine HCl and 2-hydroxypropyl-β-cyclodextrin two weeks after preparation.

A DSC test was carried out on the complex of Example 8 two weeks after preparation. The thermogram (FIG. 6) shows absence of thermal events at temperatures below 200° C.

iv) Complex of Example 9

A DSC test was carried out on the complex of Example 9 two weeks after preparation.

Figure 7:
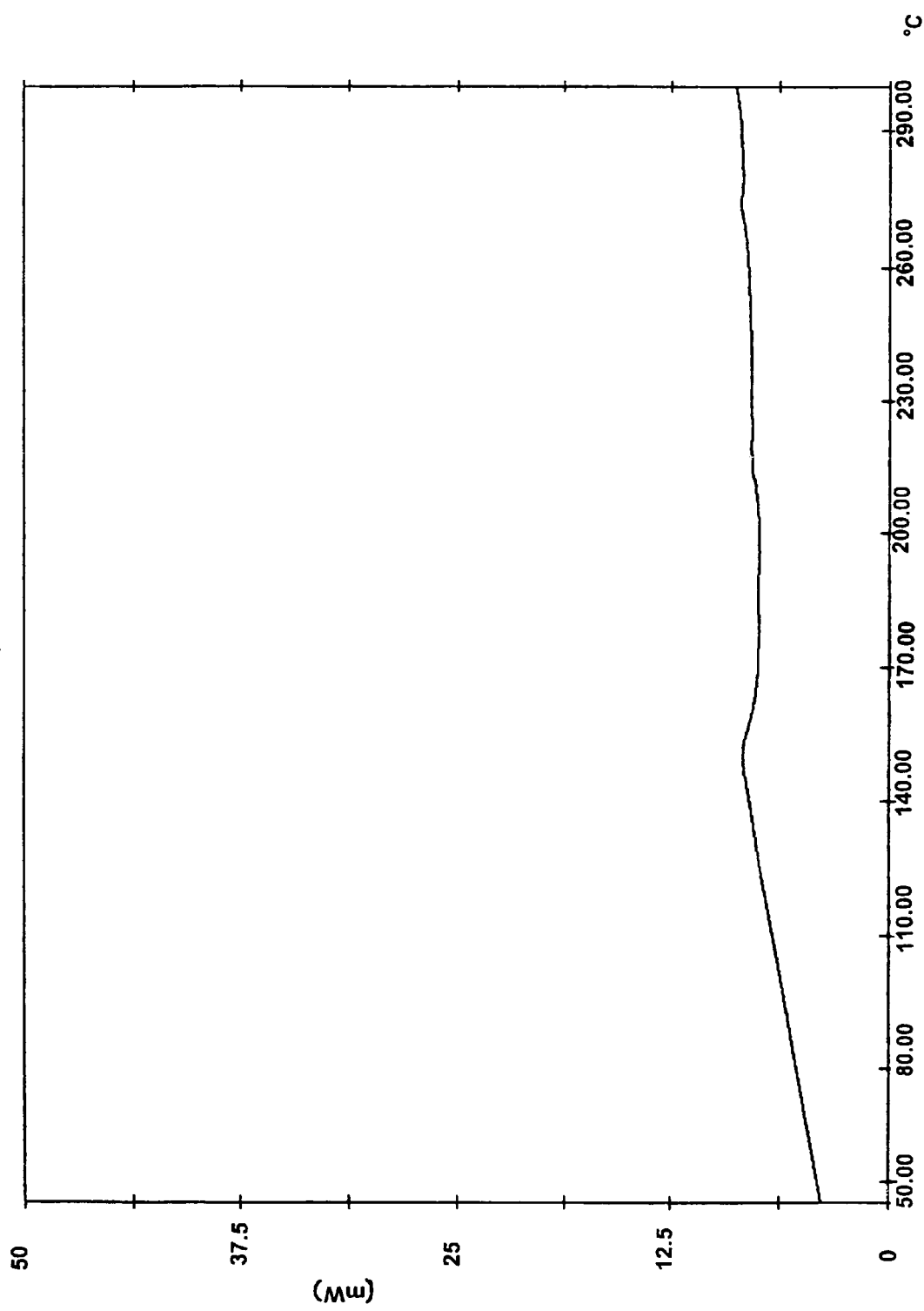
FIG. 7 shows the thermogram obtained in a DSC test carried out on a complex between paroxetine base and β-cyclodextrin two weeks after preparation.

The thermogram is reported in the FIG. 7. One may notice the absence of the decomposition peak between 260° C. and 300° C. characteristic of paroxetine base, as a demonstration of the occurred complexation.

D) X-ray Diffraction

Samples of 200 mg of the products obtained in Example 1 and in Example 6 have been analysed by X-ray diffraction using a PW 3710 difractometer (Philips Analytical X-Ray B.V.)

Figure 8:
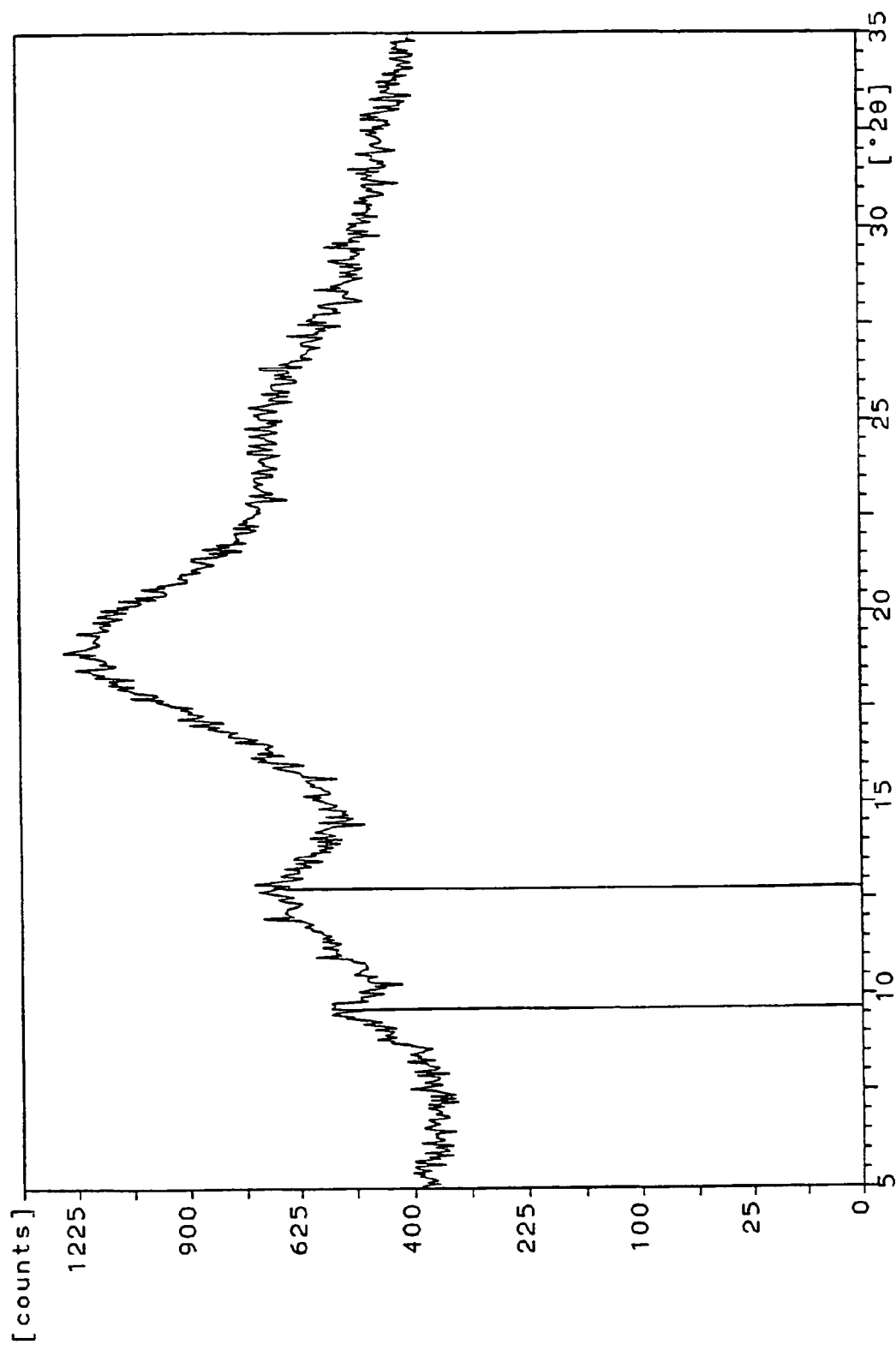
FIG. 8 shows a X-ray spectrum of a complex between paroxetine HCl and β-cyclodextrin, wherein the complex has been prepared according to Example 1.
Figure 9:
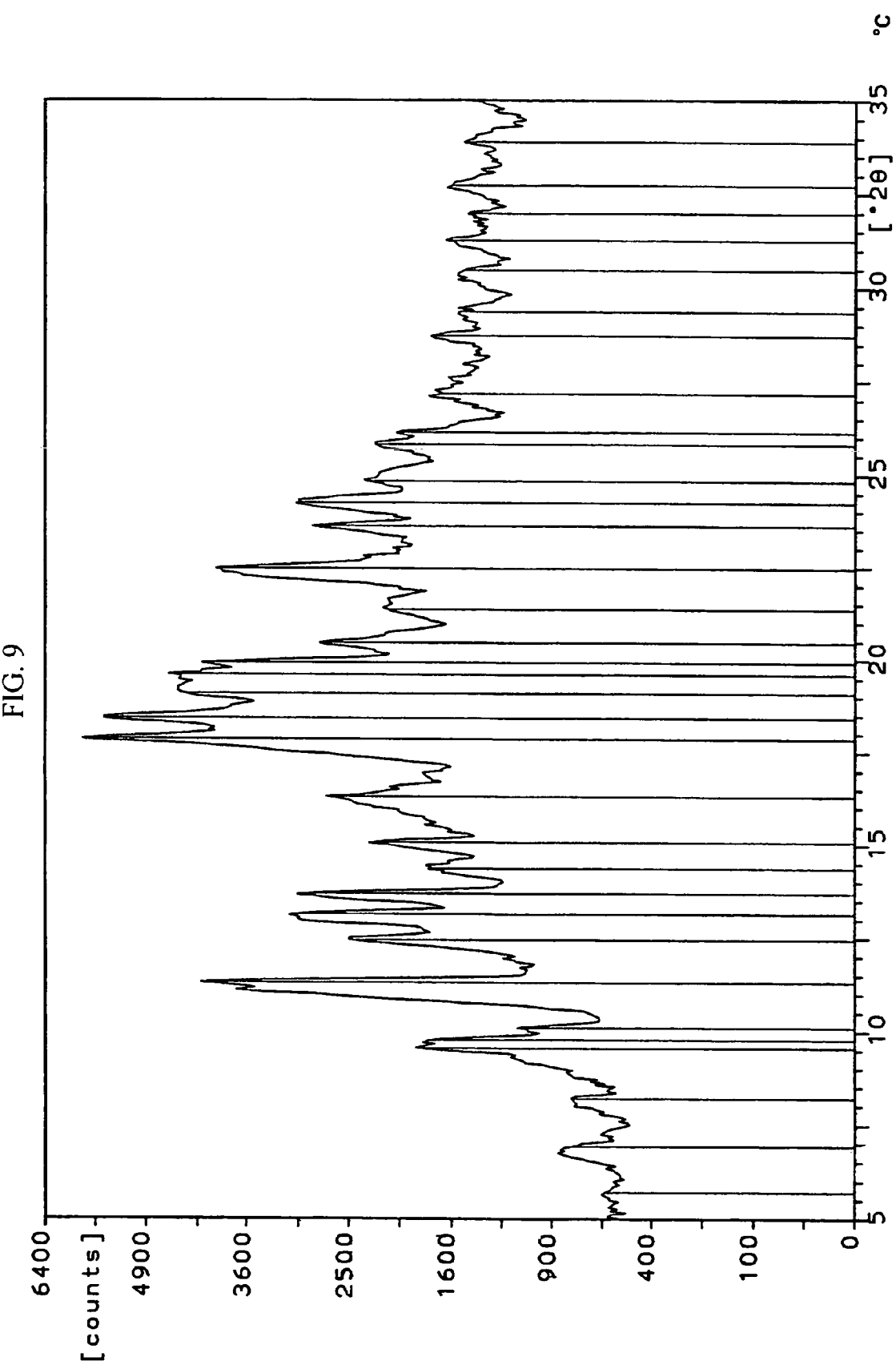
FIG. 9 shows a X-ray spectrum of a complex between paroxetine HCl and β-cyclodextrin, wherein the complex has been prepared according to Example 6.

The obtained spectra show that different drying procedures lead to complexes having different characteristics. In fact, while an amorphous complex containing paroxetine HCl is obtained in Example 1 by freeze drying (FIG. 8), a crystalline complex containing paroxetine HCl is obtained in Example 6 by vacuum drying (FIG. 9).

E) Stability Evaluation i) Compression Behaviour

About 50 mg of the product obtained as described in Example 1 were compressed in an infrared press at a pressure of 10 T for 5 minutes.

Figure 10:
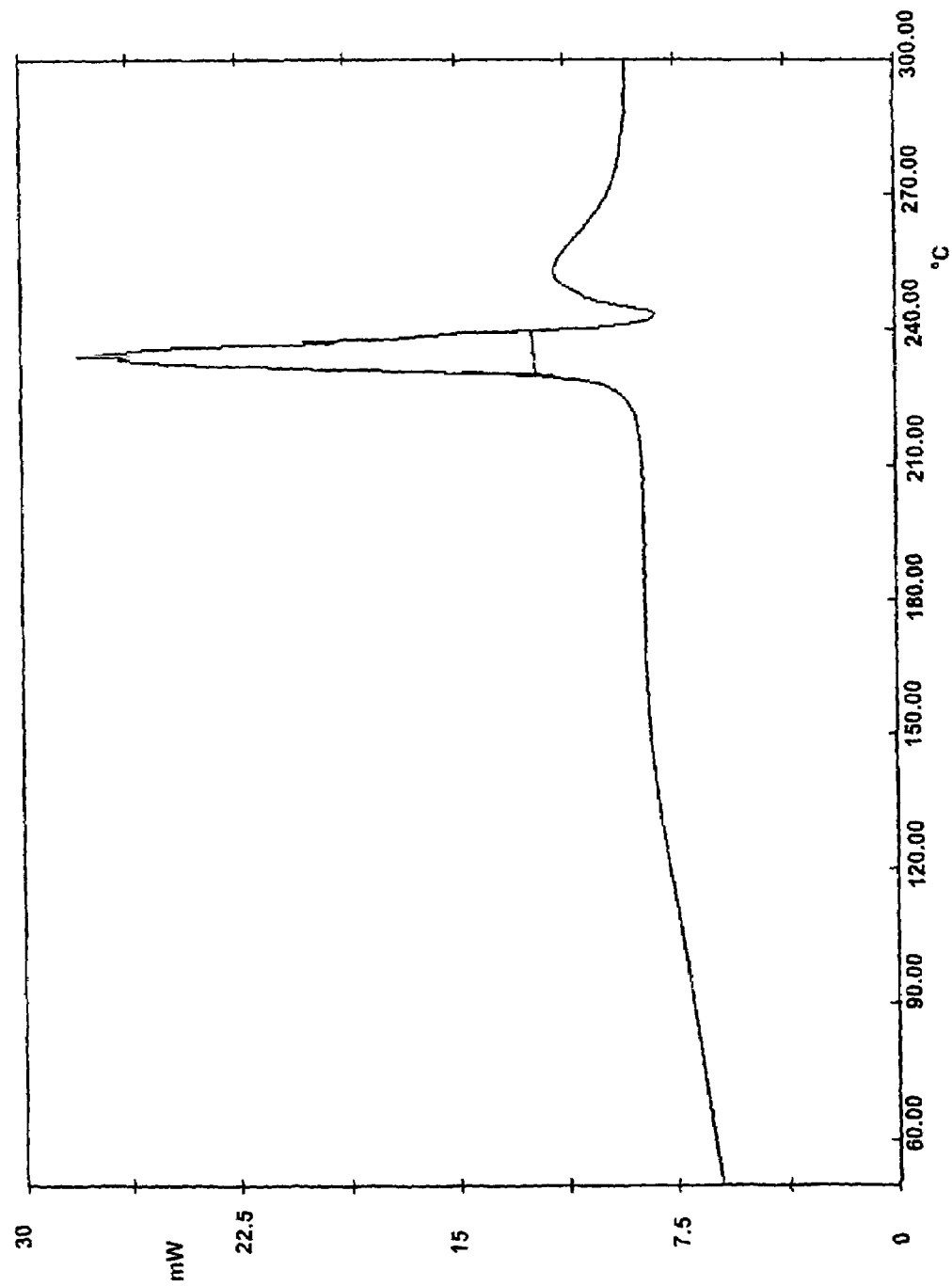
FIG. 10 shows the thermogram obtained in a DSC test carried out on a complex between paroxetine HCl and β-cyclodextrin immediately after compression in an infrared press.
Figure 11:
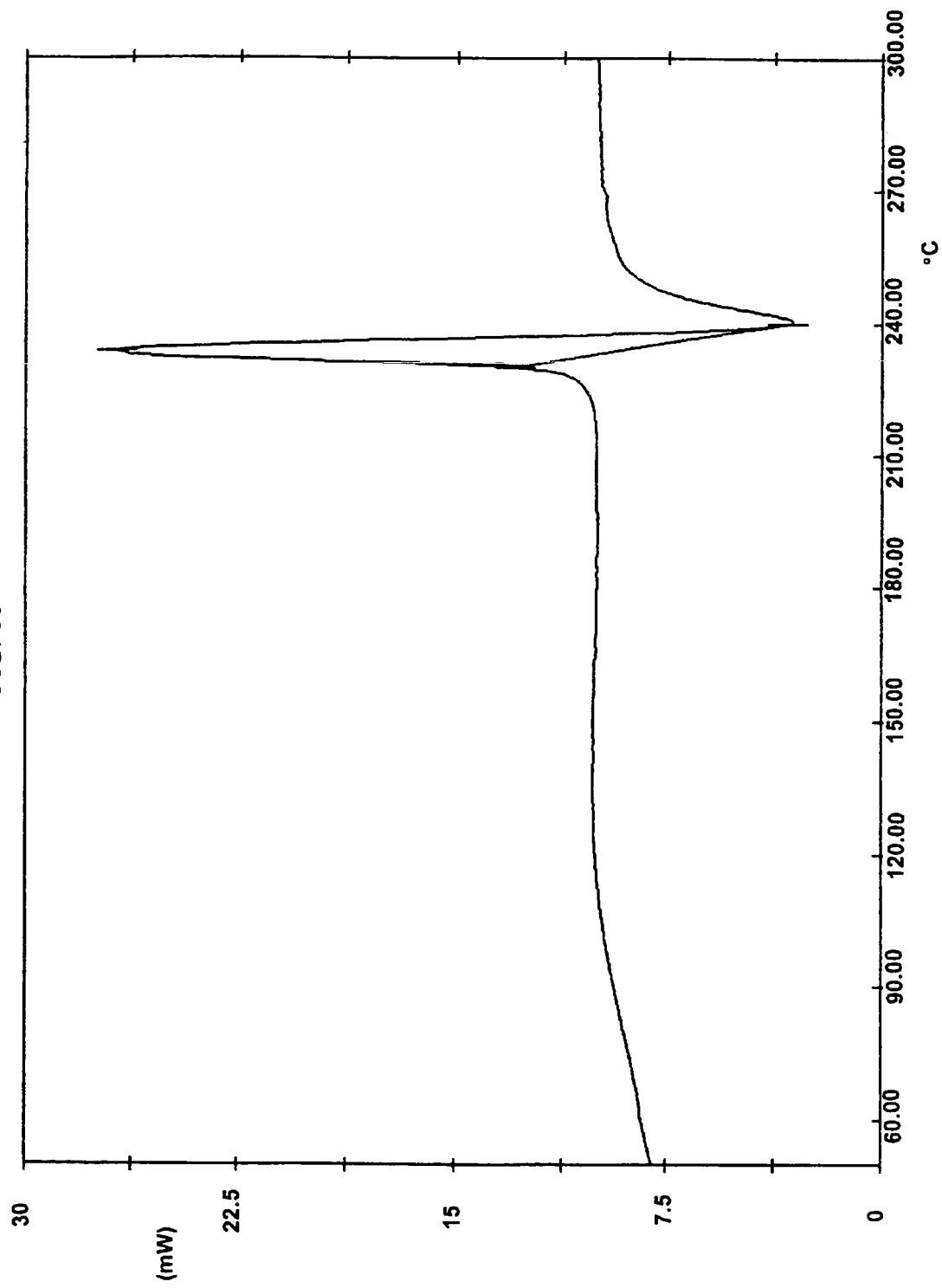
FIG. 11 shows the thermogram obtained in a DSC test carried out on a complex between paroxetine HCl and β-cyclodextrin three days after compression in an infrared press.

FIG. 10 shows the thermogram (DSC) carried out immediately after compression and FIG. 11 shows the thermogram carried out 3 days from compression, after storing at room temperature.

Also this test confirms the stability of the product which is not transformed by pressure to known forms of paroxetine HCl.

ii) Chemical Stability

The product of Example 1 has been tested using accelerated stability tests. Samples of the product as a solid or in solution (at a concentration of 4 mg/ml of paroxetine HCl) were stored for one month at 40° C. As a reference, at the same time equivalent samples were stored at 4° C.

Quantitative determination of paroxetine HCl was carried out by HPLC.

The results obtained show that the drug does not undergo any alteration in the above reported conditions.

iii) Stability at 60° C.

About 200 mg of paroxetine base and 1 g of the complex of Example 9 (corresponding to about 180 mg of paroxetine base) have each been introduced in a neutral white glass containers and stored, opened, in an oven at 60° C.

The product in the two containers has been visually examined after 48 hours of storage.

The results are reported in the following table:

TABLE 4

| | Paroxetine base | Paroxetine base-β-cyclodextrin |
|---|---|---|
| Initial | Straw-Yellow liquid | White powder |
| 48 h 60° C. | Brown liquid | White powder |

The results obtained show that the incorporation of paroxetine base into β-cyclodextrin stabilises the active principle.

F) IGROSCOPICITY

The water content of the product of Example 1 before and after the treatment described below has been determined using the Karl Fisher method.

The product of Example 1 was sieved through a 600 μm sieve in order to obtain an homogeneous powder and weighed exactly in an open glass crucible.

The crucible was put in a climatic chamber at 25° C. with 60% relative humidity for 2 or 7 days and then weighed again. The percentage of water absorbed was estimated by weight difference with respect to the initial weight. The results obtained are reported in Table 5.

TABLE 5

| Time | Water content (% by weight) |
|---|---|
| 0 | 5.4 |
| 2 days | 10.5 |
| 7 days | 11 |

EXAMPLE 13

Tablets having the following composition:

| | |
|---|---|
| Product of Example 6 | 98 mg |
| Calcium Phosphate | 259 mg |
| Sodium Starch Glycolate | 2 mg |
| Magnesium Stearate | 3 mg | were prepared by direct compression using a rotary press with a 9 mm punch.

A taste masking coating and a gastro-enteric coating were achieved by applying respectively 2 mg/cm² of a blend of methacrylic acid copolymer/Sodium Carboxymethylcellulose and 1.5 mg/cm² of a methacrylic acid copolymer.

A dissolution test was performed on the tablets described above and on commercially available tables of non-complexed paroxetine HCl hemihydrate, all containing the same amount of active principle.

The test was carried out according to European Pharmacopeia, 3$^{rd}$ Ed. 1997, 2.9.3 page 128, using the following conditions:

| | |
|---|---|
| Apparatus: | Paddle |
| Medium: | HCl 0.1 N or Phosphate Buffer pH 6.8 |
| Stirring speed: | 60 rpm |
| Temperature: | 37° C. |

The percentage of paroxetine HCl dissolved was evaluated at 5, 15, 30 and 60 minutes by UV detection at 294 nm, using paroxetine HCl as a standard.

The results obtained in HCl 0.1 N are reported in Table 6 while the results obtained in Phosphate Buffer are reported in Table 7. The values indicated a re the average values obtained from three determinations.

TABLE 6

| Time | Taste masked tablets | Gastro-enteric coated tablets | Commercially available tablets |
|---|---|---|---|
| 0 | 0 | 0 | 0 |
| 5 | 25.4 | 0 | 31.6 |
| 15 | 64.7 | 0.3 | 68.4 |
| 30 | 89.9 | 1.2 | 93.7 |
| 60 | 100 | 2.5 | 100 |

TABLE 7

| Time | Taste masked tablets | Gastro-enteric coated tablets | Commercially available tablets |
|---|---|---|---|
| 0 | 0 | 0 | 0 |
| 5 | 30.6 | 33.9 | 17.1 |
| 15 | 64.5 | 64.9 | 29.3 |
| 30 | 75.9 | 81.9 | 42 |
| 60 | 82.8 | 87.5 | 58.1 |

The results obtained demonstrate that the solubility of the complex of paroxetine HCL-β-cyclodextrin is independent from the pH of the medium when formulated as taste masked tablets. Furthermore, when the complex is formulated as a gastro-protected tablet it shows a suitable dissolution behaviour in intestinal environment.

EXAMPLE 14

A formulation in drops comprising the product of Example 6 was prepared, having the following composition:

| | |
|---|---|
| Product of Example 6 | 98 mg |
| Sucrose | 100 mg |
| Flavour | 50 mg |
| Depurated water to | 1 ml. |

The formulation has a concentration of paroxetine-HCl-β-cyclodextrin of 20 mg/ml and it is stable for up to 1 month of storage at 40° C.

What is claimed is:

1. An inclusion complex of paroxetine, as a free base or as a salt, with a cyclodextrin.

2. The inclusion complex as claimed in claim 1, wherein it is in the form of a flowing powder, it has a greater stability in comparison with the non-complexed paroxetine, organic solvents are absent, it has a higher solubility in water with respect to the non-complexed paroxetine and a DSC profile different from that of the corresponding non-complexed paroxetine or paroxetine salt.

3. The inclusion complex as claimed in claim 2, wherein ethanol is absent.

4. The inclusion complex as claimed in claim 1, having a water content of between 1 and 20% by weight.

5. The inclusion complex as claimed in claim 4, having a water content between 2 and 15% by weight.

6. The inclusion complex as claimed in claim 1, wherein the cyclodextrin is selected from the group consisting of α, β and γ-cyclodextrin.

7. The inclusion complex as claimed in claim 6, wherein the cyclodextrin is a β-cyclodextrin.

8. The inclusion complex as claimed in claim 1, wherein the salt of paroxetine is a salt with an organic or inorganic acid.

9. The inclusion complex as claimed in claim 8, wherein said organic or inorganic acid is selected from the group consisting of acetic acid, maleic acid, hydrochloric acid and methanesulfonic acid.

10. The inclusion complex as claimed in claim 9, wherein said acid is hydrochloric acid.

11. The inclusion complex as claimed in claim 1, wherein the molar ratio between paroxetine and said cyclodextrin ranges from 1:0.25 to 1:20.

12. The inclusion complex as claimed in claim 11, wherein the molar ratio between paroxetine and said cyclodextrin ranges from 1:0.5 to 1:2.

13. A pharmaceutical composition containing as an active substance a pharmaceutically effective dose of an inclusion complex as defined in claim 1, in mixture with pharmaceutically acceptable diluents or excipients.

14. The pharmaceutical composition as claimed in claim 13 in solid or liquid form, for oral and for parenteral administration.

15. An inclusion complex of paroxetine, as a free base or as a salt, with a cyclodextrin derivative, wherein said inclusion complex is in the form of a flowing powder, has a greater stability in comparison with the non-complexed paroxetine, is free from organic solvents, has a higher solubility in water with respect to the non-complexed paroxetine and a DSC profile different from that of the corresponding non-complexed paroxetine or paroxetine salt, and wherein said cyclodextrin derivative is selected from the group consisting of heptakis (2,6-di-O-methyl)-β-cyclodextrin, heptakis (2,3,6-tri-O-methyl)-β-cyclodextrin, monosuccinyl-heptakis( 2,6-di-O-methyl)-β-cyclodextrin, 2-hydroxypropyl-β-cyclodextrin, sulfated cyclodextrin and cyclodextrin containing aminoalkyl groups.

16. The inclusion complex as claimed in claim 15, wherein ethanol is absent.

17. The inclusion complex as claimed in claim 15, wherein said salt of paroxetine is a salt with an organic or inorganic acid.

18. The inclusion complex as claimed in claim 15, wherein said organic or inorganic acid is selected from the group consisting of acetic acid, maleic acid, hydrochloric acid and methanesulfonic acid.

19. The inclusion complex as claimed in claim 18, wherein said acid is hydrochloric acid.

20. The inclusion complex as claimed in claim 15, wherein the molar ratio between paroxetine and said cyclodextrin derivative ranges from 1:0.25 to 1:20.

21. The inclusion complex as claimed in claim 20, wherein the molar ratio between paroxetine and said cyclodextrin derivative ranges from 1:0.5 to 1:2.

22. The inclusion complex as claimed in claim 15, wherein said cyclodextrin derivative is the 2-hydroxypropyl-β-cyclodextrin.

23. A pharmaceutical composition containing as an active substance a pharmaceutically effective dose of an inclusion complex as defined in claim 15, in mixture with pharmaceutically acceptable diluents or excipients.

24. The pharmaceutical composition as claimed in claim 23, in solid or liquid form, for oral and for parenteral administration.

\* \* \* \* \*